United States Patent [19]
Tsuboi et al.

[11] Patent Number: 5,777,228
[45] Date of Patent: Jul. 7, 1998

[54] METHOD AND APPARATUS FOR MEASURING CHANGE IN STATE OF OBJECT TO BE MEASURED USING FLEXURAL AND TORSIONAL VIBRATIONS

[75] Inventors: Kiyoshi Tsuboi, Musashino; Shigeharu Yamamoto, Yokohama, both of Japan

[73] Assignees: Iwatsu Electric Co., Ltd.; All Nippon Airways Co., Ltd., both of Tokyo, Japan

[21] Appl. No.: 805,299

[22] Filed: Feb. 25, 1997

Related U.S. Application Data

[62] Division of Ser. No. 646,067, May 7, 1996, Pat. No. 5,696,324.

[30] Foreign Application Priority Data

May 11, 1995 [JP] Japan ................................. 7-137293
May 11, 1995 [JP] Japan ................................. 7-137294
May 11, 1995 [JP] Japan ................................. 7-137295
Apr. 19, 1996 [JP] Japan ................................. 7-122218

[51] Int. Cl.$^6$ ................................................ G01N 29/04
[52] U.S. Cl. ........................... 73/579; 73/602; 364/508
[58] Field of Search ........................... 364/506, 507, 364/512, 563; 73/579, 583, 602

[56] References Cited

U.S. PATENT DOCUMENTS 5,060,516 10/1991 Lau ........................................... 73/579

*Primary Examiner*—Christine K. Oda
*Attorney, Agent, or Firm*—Finnegan, Henderson, Farabow, Garrett & Dunner

[57] ABSTRACT

A method and apparatus for detecting a change in the state of a part of an object to be measured that has a section having a first plate part and a second plate part which has a plate surface opposite to a plate surface of the first plate part with a gap between the plate surfaces and is integral with the first plate part or is connected to the first plate part. The method includes, and the apparatus has device for, applying vibrations to the object to be measured at a site at the section to generate flexural, torsional and stationary vibration waves in the object, subjecting the stationary vibration waves generated in the object to be measured to a spectral analysis, calculating the frequency difference of spectra divided into two by high order torsional vibrations generated at the section out of the group of spectra by the stationary vibration waves, and detecting a change in thickness between the first plate part and the second plate part or a defect formed in the first plate part or the second plate part based on the calculated frequency difference.

4 Claims, 11 Drawing Sheets (W₁)

5,777,228

METHOD AND APPARATUS FOR MEASURING CHANGE IN STATE OF OBJECT TO BE MEASURED USING FLEXURAL AND TORSIONAL VIBRATIONS

This application is a division of application Ser. No. 08/646,067 filed May 7, 1996, Pat. No. 5,696,324.

BACKGROUND OF THE INVENTION

1. Field of the Invention

This invention relates to a method and apparatus for detecting a defect formed at an intersection part of a united part of an object to be measured which has two plate parts having one section with the plate surfaces opposite to each other and other section that is united integrally with said one section or is bonded to said one section with the other section having the intersection part to said plate part, such as a turbine blade used in a turbine engine.

Further, this invention also relates to a method and apparatus capable of detection of a change in thickness of two plate parts due to a change in the state of plate surfaces of the two plates sections of an object to be measured, such as a turbine blade, which has a section with the plate surfaces of the two plate parts opposite to each other with a gap between them, such as a turbine blade used in a turbine engine mentioned above.

Further, this invention relates to a method and apparatus for predicting the life of an object to be measured by detecting the degree of deterioration of a section of the object to be used that is mainly used thereby enabling the life of the particular object to be measured to be predicted.

2. Description of the Prior Art

If a structure, such as a machine and a part of a product, has a defect, such as a crack, a cavity called "su" in Japanese, or a recess, there is a risk that leads to various inconveniences, and therefore it is desired that the part having a defect, such as a crack, a cavity, and a recess, is eliminated by detecting the presence of such a defect in advance.

Heretofore, as means of detecting a crack or the like, nondestructive inspection methods are known. Nondestructive inspection methods that are now available include, for example, an ultrasonic wave reflection method of detecting defects by using ultrasonic waves reflected, a so-called AE (acoustic emission) detection method based on sounds attributable to the formation of a crack, an observation method using a CCD camera, an X-ray photograph method, and a color check method.

Meanwhile, with respect to structures, such as parts, there are many structures that have a part in the shape with two platelike items bonded together (including the case wherein two platelike items are integrally constructed) in order to make it light or to provide the inside thereof with a flow passage for a gas or a liquid.

For instance, the blade part of a turbine blade of a turbine engine of an airplane has a structure that two opposite platelike items with a gap between them are connected through bridge sections. The spaces partitioned by the bridge sections are constructed to serve as flow passages for heated air.

The turbine blade is composed of blade parts, a pedestal that is called a so-called platform part and to which the blade parts are connected, and a leg part continuous to the pedestal.

In the case of such a structure, the pedestal that is a united section joining the blade part to the leg part is in a state having an intersection part with surfaces intersecting at a prescribed angle, for example, 90°, like an L-shaped part. In this specification, the term "unite" include both "connect different sections" and "unite integrally different sections".

In such an intersection part wherein surfaces intersect like an L-shaped part, stress is concentrated in many cases, and such a section is apt to be scared. Further, in the case wherein a scar of the intersection part has penetrated into the part of the joined section, the scar in concert with the concentration of stress into the intersection part is enlarged, which will likely lead to destruction or the like of the united part, and therefore it is desirable that a scar in the intersection part can be detected separately from other sections.

However, in the case wherein a scar formed in said intersection part is probed by the above-described conventional nondestructive inspection method, it is required to probe this intersection part in a concentrated manner. In the case wherein the examination is carried out in such a manner, the ultrasonic reflection method of examining a defect is a contact method and measures only the section where a sensor is applied because of rectilinear propagation of ultrasonic waves, and therefore there are such disadvantages that the examination takes time, and judgement is not easy because of reflection of ultrasonic waves due to non-alignment in the sensor connection surface and because visible waveforms become different depending on a small angular difference of the propagation direction of ultrasonic waves.

Further, in the case of the AE method, it is a contact method like the ultrasonic reflection method of examining a defect and there is the problem that the measurement is impossible if the crack is not a linear crack. In addition, in some cases of linear cracks, it is required to carry out the measurement with the crack being increased.

Further, in the case of the observation method using a CCD camera, there is the fault that a judgement is disturbed if there is a stain or a pattern other than a crack. Further, in the case of the X-ray photograph method, although it is effective because a direct visual observation is possible, for example, there is the fault that the amount of X-ray is required to be adjusted depending on the thickness of the object to be measured and this adjustment is troublesome not to allow observation.

A first object of this invention is to provide a method and apparatus for detecting a defect that is capable of detecting quickly and easily a defect, such as a crack and a cavity, formed in an intersection part of a structure as described above without causing faults as mentioned above.

By the way, since hot air is passed through the inside of a blade part of a turbine blade, the inner wall surface thereof is oxidized. Then with the passage of the operating time, a crack and the like are formed in the oxidized section, the particular inner wall surface section comes off, and the platelike item constituting the blade part becomes thinner. Therefore, it is important to monitor the thickness of the platelike item constituting the blade part to judge the deterioration of the turbine blade or to judge the necessity of the repair.

However, if a change in the thickness of this blade part is measured by the above-mentioned conventional nondestructive inspection method, generally it takes very long time, and in some cases, even it requires to take 1 hour to measure a thickness. Further, most of the conventional nondestructive inspection methods are contact-type inspection methods wherein measurement is carried out with a sensor in contact with a site to be checked, and therefore are not suitable, for example, for judgement of a defect in the blade part.

A second object of this invention is to provide a method and apparatus that can detect quickly and easily a defect formed in the inner surface of a section which is possessed by an object to be measured and wherein two plate parts are opposed with a prescribed gap between their plate surfaces as described above and a change in thickness of the plate parts of that particular section resulted thereby.

Further, the conventional methods of detecting a defect as described above detect whether or not a defect or the like is formed in an object to be measured and are not suitable for knowing the life of an object to be measured as to ascertain how long the object to be measured can be used safely.

However, parts are gradually deteriorated by the use thereof and, for example, in the case of turbine blades used in turbine engines of airplanes described above, it is very important to predict the life thereof and prevent a serious accident from occurring by replacing it in a suitable early stage before the formation of a defect or the like.

In that case, the blade part in the turbine blade is deteriorated mainly by the use thereof and it is expected that the progress of deterioration is quicker in the blade part than in the pedestal called the platform part to which the blade part is united. Therefore it is important to detect the degree of deterioration of the blade part.

A third object of this invention is to provide a method and apparatus that can predict the life of an object to be measured that has a first section which is a major working section and a second section that is united integrally with said first section or is bonded to said first section by detecting the degree of deterioration of said first section.

SUMMARY OF THE INVENTION

When vibrations are caused in an object to be measured, generally in this object to be measured, longitudinal waves (longitudinal vibrations=flexural vibration mode), transverse waves, and torsional waves (torsional vibration mode) are generated in a set. For the sake of simplifying the explanation, let's take, for example, a cylinder 1 having a diameter d and a length h as shown in FIG. 1A. Now, with respect to this cylinder 1, if a tiny unit cylinder 2 having a length Δh is imagined, and vibrations are applied to the cylinder 1, then in accordance with the vibration application position, three types of vibration waves that change the unit cylinder 2 as shown in FIGS. 1B, 1C, and 1D are generated.

That is, FIG. 1B illustrates longitudinal waves, which are waves that vibrate to change the unit cylinder 2 only in the direction of the length. The frequency of the longitudinal waves corresponds to the length h between the opposed circular end surfaces of the cylinder 1. That is, letting the speed of sound stand for c, then $$f = c \cdot n/2h \quad (1)$$

wherein n represents the order of the harmonic.

Further, FIG. 1C illustrates transverse waves, which are waves that vibrate to change the unit cylinder 2 only in the direction of the diameter d without changing the length Δh. Further, FIG. 1D illustrates torsional waves, which are waves that, when propagate from one circular end surface to the other circular end surface, result in torsional revolution about the axis of the cylinder and are generated together with the transverse waves.

The individual vibration waves described above assume respective frequencies determined in conformity with the shape and size of the object to be measured. For example, an object to be measured is vibrated at a position that excepts the centrobaric position and where longitudinal vibrations and torsional vibrations (including transverse waves in this specification) will be generated, and when the stationary vibration waves then generated in the object to be measured are picked up in a noncontact manner and are subjected to a spectral analysis, some peaks of spectra are obtained in ascending order of the frequencies.

As an object to be measured to which the defect detecting method and apparatus according to the present invention is directed so as to attain the first object mentioned above, the thing shown in FIG. 2 and FIG. 3 can be imagined. That is, as shown in FIG. 2, the object to be measured is constituted to have an upper section 1 and a lower section 2 to which a joining section 3 is, for example, bonded as shown. In this case, as shown in FIG. 3 that is a sectional view taken along line 3—3 of FIG. 2, the joining section 3 is constituted, for example, by connecting an arcuate plate 3A and a planar plate 3B.

In the case of an object to be measured that has such a structure, the uniting sections of the joining section 3 with the upper section 1 and the lower section 2 take a state having intersection parts 4 and 5 with surfaces intersecting at a prescribed angle, for example, at 90°, like an L-shaped item.

That is, this object to be measured is an object to be measured that has a first section (the joining section 3 in FIG. 2) with a first plate part (for example, the arcuate plate 3A in FIG. 2) and a second plate part (for example, the planar plate 3B in FIG. 2) that has a plate surface opposite to a plate surface of the first plate part and is integrated with said first plate part or is connected to said first plate part and a second section (the upper section 1 and the lower section 2 in FIG. 2) that is united integrally with said first section or is bonded to said first section and this object to be measured has a structure item with a structure wherein intersection parts (the intersection parts 4 and 5 in FIG. 2) are formed between the plate surface of said first and/or the second plate part of said first section and the surfaces of the uniting parts of said second part with said first section.

In the method of detecting a defect, the above object to be measured is vibrated and the stationary vibration waves generated in the object to be measured are subjected to a spectral analysis. A displacement of the frequency of the spectrum of the torsional vibration mode out of the group of spectra due to said stationary vibration waves, which displacement corresponds to the presence of a defect, is found. On the basis of this frequency displacement, a defect formed near the intersection part of said uniting part of said object to be measured is detected.

The method of detecting a defect is a method that can quantitate the magnitude of a defect formed near an intersection part, comprising detecting a defect formed near the intersection part of said uniting part of said object to be measured on the basis of the operational result of $$(f5-f4)/(f2-f1)$$

wherein f1 represents the frequency of the first order spectrum of the flexural vibration mode out of the group of spectra by said stationary vibration waves, f2 represents the frequency of the first order spectrum of the torsional vibration mode out of the group of spectra by said stationary vibration waves, f4 represents the frequency of the second order spectrum of said flexural vibration mode out of the group of spectra by said stationary vibration waves, and f5 represents the frequency of the second order spectrum of the torsional vibration mode out of the group of spectra by said stationary vibration waves.

The method of detecting a defect takes into account the case wherein a first and second plate parts are changed in thickness by the use thereof, comprising detecting a defect formed near the intersection part of said uniting section of said object to be measured on the basis of the operational result of $$\{(f5-f4)(f2-f1)\}/\{(f6-f4)(f3-f1)\}$$

wherein f1 represents the frequency of the first order spectrum of the flexural vibration mode out of the group of spectra by said stationary vibration waves, f2 represents the frequency of the first order spectrum of the torsional vibration mode out of the group of spectra by said stationary vibration waves, f3 represents the frequency of the first order spectrum of the mixed vibrations of the flexural vibration mode and the torsional vibration mode out of the group of spectra by said stationary vibration waves, f4 represents the frequency of the second order spectrum of said flexural vibration mode out of the group of spectra by said stationary vibration waves, f5 represents the frequency of the second order spectrum of the torsional vibration mode out of the group of spectra by said stationary vibration waves, and f6 represents the frequency of the second order spectrum of the mixed vibrations of the flexural vibration mode and the torsional vibration mode out of the group of spectra by said stationary vibration waves.

The method of detecting a defect according to the present invention that has the above constitution is based on the following results of studies: when the stationary vibration waves of an object to be measured out of the picked-up vibrations are subjected to a spectral analysis, peaks of a spectra appear at some natural frequency positions that are determined in accordance with the shape or the structure of the object to be measured and when attention is given to frequencies of the peaks of the spectra due to the torsional vibration mode out of them, then a defect formed at the intersection part of the object to be measured can be detected.

That is, in the case wherein a first plate part and the second plate part are opposed and combined like an object to be measured to which the present invention is directed, due to a difference in size between the first plate part and the second plate part, groups of spectra owing to three vibration modes, that is, the flexural vibration mode, the torsional vibration mode, and the mixed vibration mode of the flexural vibration mode with the torsional vibration mode appear in agreement with the respective plate parts. Out of these groups of spectra, the group of spectra lower in frequency is a group of the first order spectra and the group of spectra higher in frequency is a group of the second order spectra.

Further, in the case having no defect in an intersection part of an object to be measured and in the case having a defect in an intersection part of an object to be measured, it has been found that although a little change is observed in the frequencies f1 and f4 of the first order and second order spectra of the flexural vibration mode, a change is produced in the frequencies of the spectra of the torsional vibration mode, and particularly a frequency change that is enough to be significant is produced in the frequency f5 of the second order spectrum.

This can be considered as follows: when an object to be measured is vibrated, stationary vibration waves inherent therein are generated, and it can be observed that, due to the vibration waves, spectra at the natural vibration positions can be observed. As natural vibration waves, generally, the flexural vibration mode, the torsional vibration mode, and the vibration mode formed by mixing the flexural vibration mode with the torsional vibration mode are generated and some spectra in conformity with these vibration modes can be observed. Further, it is considered that a defect, such as a scar, formed in an intersection part does not influence so much the flexural vibration mode but influences the torsional vibration mode considerably if the order is higher.

Therefore, basically, a defect at an intersection part of an object to be measured can be detected if a frequency difference between the frequency of the spectrum of the flexural vibration mode and the frequency of the spectrum of the torsional vibration mode out of the groups of the first order spectra, the second order spectra, and so on.

However, according to the results of study, it has been found that although the influence of the presence of a defect, such as a scar, formed at an intersection part of an object to be measured on the frequency f2 of the first order spectrum of the torsional vibration mode is little and is not so different from that of the case free of a defect, the influence of the presence of a defect, such as a scar, formed at an intersection part of an object to be measured on the frequency f5 of the secondary spectrum of the torsional vibration mode is relatively large and the frequency f5 is shifted higher than the case free of a defect.

Therefore, practically, if the difference $\Delta f45=f5-f4$, i.e., the difference between the frequency f4 of the spectrum of the flexural vibration mode and the frequency f5 of the spectrum of the torsional vibration mode, is found and is monitored, a defect in an intersection part can be detected.

In the case wherein the formation and the size of a defect at an intersection part of an object to be measured are measured precisely and quantitatively, as described above for the present invention, it is enough to use the calculation of the ratio of the above $\Delta f45$ to the frequency difference $\Delta f12=f2-f1$, i.e., the difference between the frequency f1 of the spectrum of the flexural vibration mode and the frequency f2 of the spectrum of the torsional vibration mode, out of the group of the first order spectra, that is, $$\Delta f45/\Delta f12=(f5-f4)/(f2-f1)$$

The result of this operation has a value in proportion to the size of the defect.

In the case having a first plate part and a second plate part as in an object to be measured to which this invention is directed, it has been found that when the thickness of the plate part becomes thin by the use of the object to be used, it affects the frequencies f1 to f6, and therefore it has been found that under such circumstances the above operational formula for detecting a defect cannot effect precise judgement.

However, this fault can be overcome as follows: attention being given to the above frequencies f3 and f8, they correspond to a change in thickness of the first plate part and the second plate part, and when the plate part becomes thin, the frequency difference between the frequency f1 and the frequency f4 does not change, but the frequencies are shifted lower as a whole, and the frequency difference between the frequency f1 and the frequency f3 and the frequency difference between the frequency f4 and the frequency f6 correspond to the thickness of the plate part. Therefore, in the present invention, a defect is detected quantitatively using, instead of the above operational formula, the following operational formula:

$$\{(f5-f4)(f2-f1)\}/\{(f6-f4)(f3-f1)\}$$

Now, the method of detecting a change in state of a part of an object to be measured is described.

This invention has been thought up based on the results of the following studies: when an object to be measured that has a section having two opposed plate parts with a prescribed gap between their plate surfaces as described above is vibrated, the vibrations of the object to be measured that have been generated as a result are picked up in a noncontact manner, and out of the picked-up vibrations the stationary vibration waves of the object to be measured are subjected to a spectral analysis, peaks of spectrums appear at some natural frequency positions determined in conformity with the shape or the structure of the object to be measured. Attention being given to higher-order spectra of the torsional type vibrations out of the peaks of plural spectra, spectra are divided into two on the basis of a difference in thickness between the two plate parts of said section of the object to be measured. Further it has been found the frequency difference $\Delta fs$ of the two spectra corresponds to a difference in thickness between the two plate parts.

This is assumed due to the fact that, in the torsional type vibrations, the frequency of the vibrations becomes higher in a thicker plate than a thinner plate. Therefore, if peeling occurs in the plate part due to the formation of a crack (an omission), since the thickness of the plate of that section becomes reduced accordingly, the above frequency difference $\Delta fs$ is increased. Accordingly, by monitoring the above frequency difference $\Delta fs$, it becomes possible to detect a change in difference in thickness between said two plate parts.

Therefore, the method of detecting a change in state of a part of an object to be measured according to the present invention is characterized by applying vibrations to such an object to be measured at a site where flexural type and torsional type vibrations will be generated at the above-described section, subjecting the stationary vibration waves generated in said object to be measured to a spectral analysis, calculating the frequency difference $\Delta fs$ of the spectra divided into two by higher-order vibrations of the torsional type vibrations generated at said section out of the group of spectra by said stationary vibration waves, and detecting a change in thickness between said first plate part and said second plate part or a defect formed in said first plate part or said second plate part on the basis of the thus calculated frequency difference $\Delta fs$.

If there has happened a change in the relationship between the thicknesses of the first and second plate parts of said section of an object to be measured due to some cause, the change in thickness is reflected, as a change in relative thickness of the first and second plate part, in a change of said frequency difference $\Delta fs$.

For example, if originally the first and second plate parts have thicknesses that are approximately equal to each other, and when a defect, such as a crack, has been formed in one of them and as a result that particular part has peeled off, the larger the extent of the peeling is, the larger said frequency difference $\Delta fs$ becomes due to a change in thickness between said first and second plate parts. Accordingly, by monitoring the frequency difference $\Delta fs$, the formation of a defect proportional in extent to the frequency difference $\Delta fs$ can be detected.

Further, if the outer surfaces of the two plate parts have been scraped and have become thin to bring about a difference in thickness between that particular two plate parts, of course the difference in thickness can be detected according to this invention.

Next, the method of predicting the life of an object to be measured according to the present invention is described.

In the results of the spectral analysis of the stationary vibration waves obtained by vibrating an object to be measured, if attention is given to the frequency difference $\Delta fc$ between the frequency of the nth-order spectrum of longitudinal waves and the frequency of the (n+1)th-order spectrum, this frequency difference $\Delta fc$ correspond to deterioration of the object to be measured in a ratio of 1 to 1, and as the deterioration progresses, the frequency difference $\Delta fc$ increases exponentially.

This can be considered as follows.

That is, by vibrating an object to be measured, stationary wave vibrations inherent therein are generated, and due to the vibrations, as described above, the first-order spectrum, the second-order spectrum, and so on can be observed at the natural frequency positions determined in accordance with the shape and the size of the object to be measured. If the degree of the deterioration of the object to be measured remains the same, the frequency positions of the respective spectra remains almost the same.

However, generally as deterioration of an object to be measured progresses, grains constituting the material becomes coarse or hardens. Further, if the deterioration progresses more than a prescribed extent and the degree of the coarseness exceeds a threshold value or if the object is a cast item or the like, a crack (an omission) is formed as segregation of graphite progresses.

If grains are made coarse or hardened, the speed of sound waves propagating through the substance is increased, and the higher the order of the vibrations is, the more it is shifted to a higher frequency. For this reason, it is considered that the frequency difference $\Delta fc$ between the frequency of the nth-order spectrum and the frequency of the (n+1)th order spectrum becomes larger as the deterioration progresses. Therefore, it is considered that, by monitoring this frequency difference $\Delta fc$, the deterioration of an object to be measured can be detected to predict the life.

Incidentally, the life of an object to be measured is preferably determined by the deterioration of the section that is used mainly. However, generally an object to be measured has a structure wherein the section that is used mainly is united to other section, such as a pedestal and a base. Accordingly, it is desired that the deterioration of the section that is used mainly can be detected with the influence due to a small crack, a hole, or the like formed in a pedestal or a base eliminated.

According to the study done by the inventors of the present invention, it has been seen that longitudinal waves are less affected by a defect, such as a crack, than torsional vibration waves. Further, it has been found that higher-order longitudinal waves are less affected by a defect.

Therefore, it is considered that an object to be measured is vibrated at the section that is used mainly, a spectral analysis as described above is carried out, and the frequency difference $\Delta fc$ between the higher-nth-order spectrum and the (n+1)th-order spectrum is detected. However, when an object to be measured is vibrated and the vibration waves are picked up and subjected to a spectral analysis, the energy of the lower-order spectrum is large and the higher-order spectrum becomes difficult to be detected.

The inventors of this invention have studied further and found that by vibrating not the section that is used mainly but a pedestal or a base to which the section that is used mainly is united, a higher-order spectrum with respect to the vibration waves of the section that is used mainly can be obtained stably.

The method of predicting the life of an object to be measured according to the present invention is based on the results of the above studies and is a method of predicting the life of an object to be measured that has a first section that is used mainly and a second section which is integrally united to said first section or is bonded to said first section by detecting the deterioration of the object to be measured, comprising applying vibrations to said object to be measured at said second section of said object to be measured, subjecting the stationary vibration waves generated in said object to be measured to a spectral analysis, and detecting the degree of deterioration of said first section of said object to be measured by a change in the frequency difference between the frequency of the nth-order (wherein n is an integer of 2 or more) of longitudinal waves and the frequency of the (n+1)-order spectrum out of the group of spectra by said stationary vibration waves, thereby predicting the life of said object to be measured.

DETAILED DESCRIPTION OF PREFERRED EMBODIMENT

Now the present invention is described with reference to the drawings. The embodiment described below is an example of the case wherein an object to be measured is a turbine blade of an engine of an airplane.

The inventors of this invention have studied the presence or absence of any defect at an intersection part of a turbine blade made of a material whose major component is titanium. First, the structure of the turbine blade to which this example is directed is described.

Figure 1A:
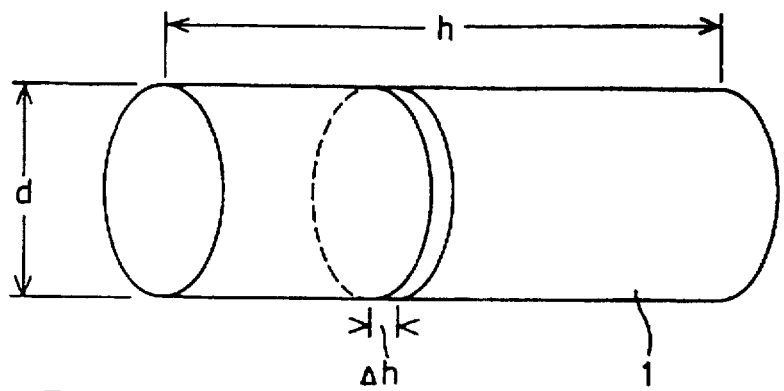
FIGS. 1A–1D are views illustrating stationary-wave vibrations that are generated in an object to be measured.
Figure 1B:
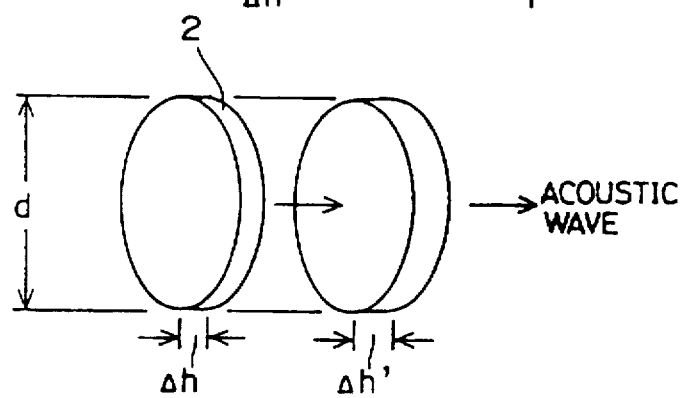
Figure 1C:
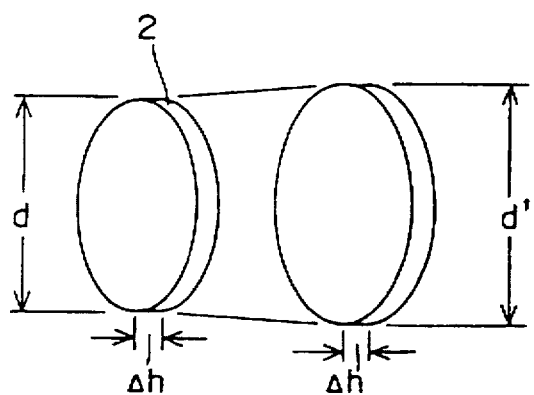
Figure 1D:
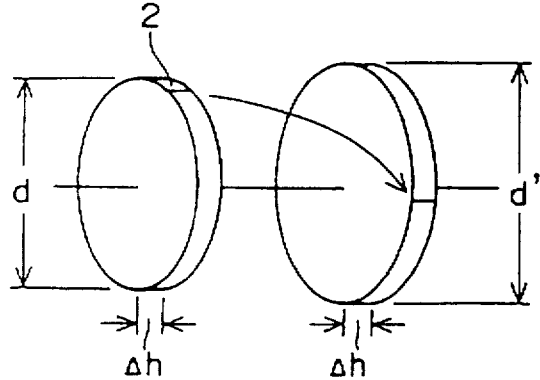
Figure 2:
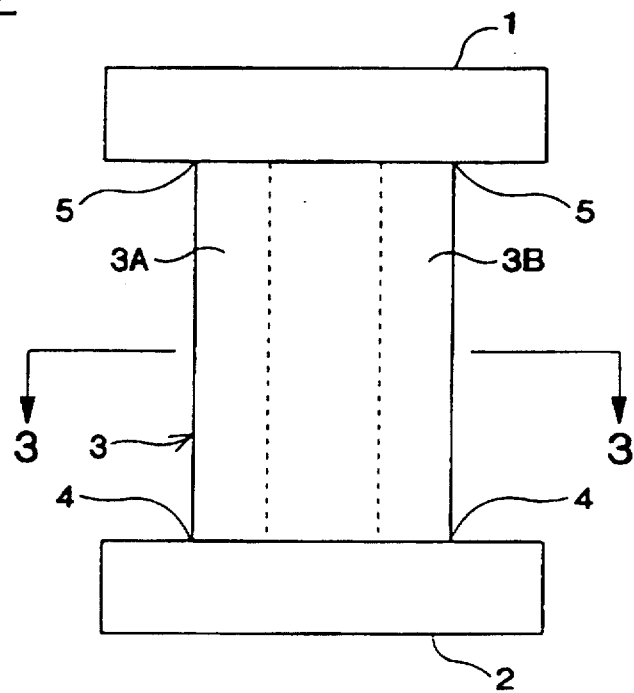
FIG. 2 is a view illustrating an example of an object to be measured in accordance with the present invention.
Figure 3:
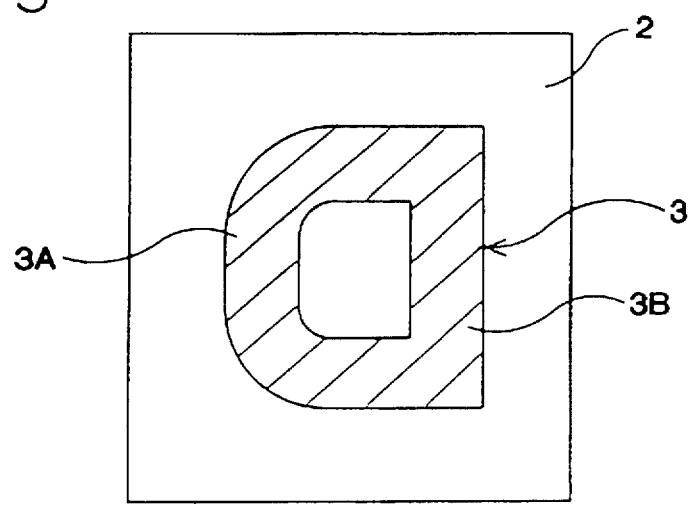
FIG. 3 is a sectional view taken along line 3—3 of FIG. 2.
Figure 4A:
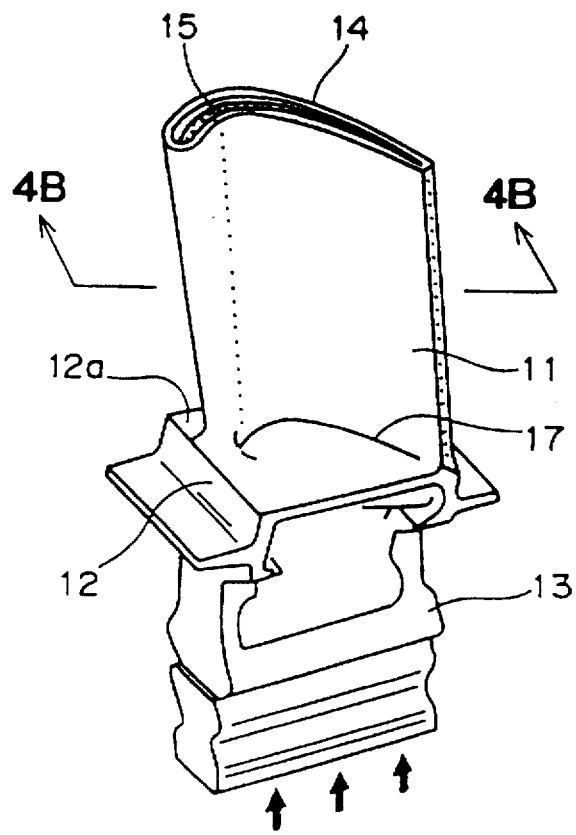
FIGS. 4A and 4B are views illustrating an example of an object to be measured in accordance with the present invention.
Figure 4B:
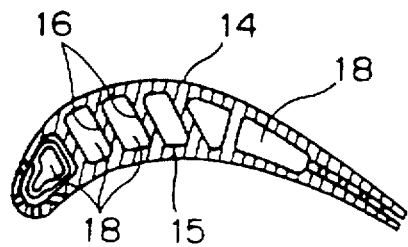

That is, the turbine blade of this example has, for instance, the shape and structure as shown in FIGS. 4A and 4B is a perspective view of the turbine blade and FIG. 4B is a cross-section (taken along line 4B—4B of FIG. 4A) of its blade section. As shown in FIGS. 4A and 4B, the turbine blade is composed of a blade part 11, a platform part 12 to which the blade part 11 is connected, and a leg part 13 continuous to the platform part 12 and is generally cast.

In this case, the turbine blade is not solid but is equipped with hollow parts 18, as is shown in FIG. 4B, which serve as passages for allowing the air, which has been fed into the inside of the blade part 11 from the side of the leg part 13 as is shown by the arrows in FIG. 4A, to be discharged out of the blade part 11.

As is shown in cross-section in FIG. 4B, the blade part 11 is constructed generally in a streamlined form and has therein the hollow parts 18 in communication with the hollow part of the leg 13, so that the blade part 11 has a structure with two plate parts 14 and 15 having streamlined surfaces that are combined and opposed with a prescribed space between them. The plate part 14 and the plate part 15 of the blade part 11 are joined by bridge parts 16 so as to form the hollow parts 18.

Parenthetically, although the blade part 14 may have the plate part 14 and the plate part 15 connected through the bridge sections 16 or may be formed monolithically as a whole, generally the blade part 14 is produced separately from the platform part 12. The turbine blade is constructed in such a way that the blade part 11 is connected to a surface 12a of the platform part 12 with the directions of the plate surfaced of the plate part 14 and the plate part 15 orthogonal to the surface 12a. Therefore, at the connection part between the blade part 11 and the platform part 12, there are present an intersection part 17 between the surface 12a and the plate surface of the plate part 12 and an intersection part 17 between the surface 12a and the plate surface of the plate part 15.

Herein, in this case, the plate part 14 and the plate part 15 are non-defectives and their thicknesses are approximately equal in the initial working state. Although the plate part 14 and the plate part 15 are equal in length in their height, generally the length of the curve of the curved surface of the plate part 14 and the length of the curve of the curved surface of the plate part 15 along the surface 12a of the platform part 12 are different. In other words, generally the plate part 14 and the plate part 15 are different in the area of their plate surfaces.

Figure 5:
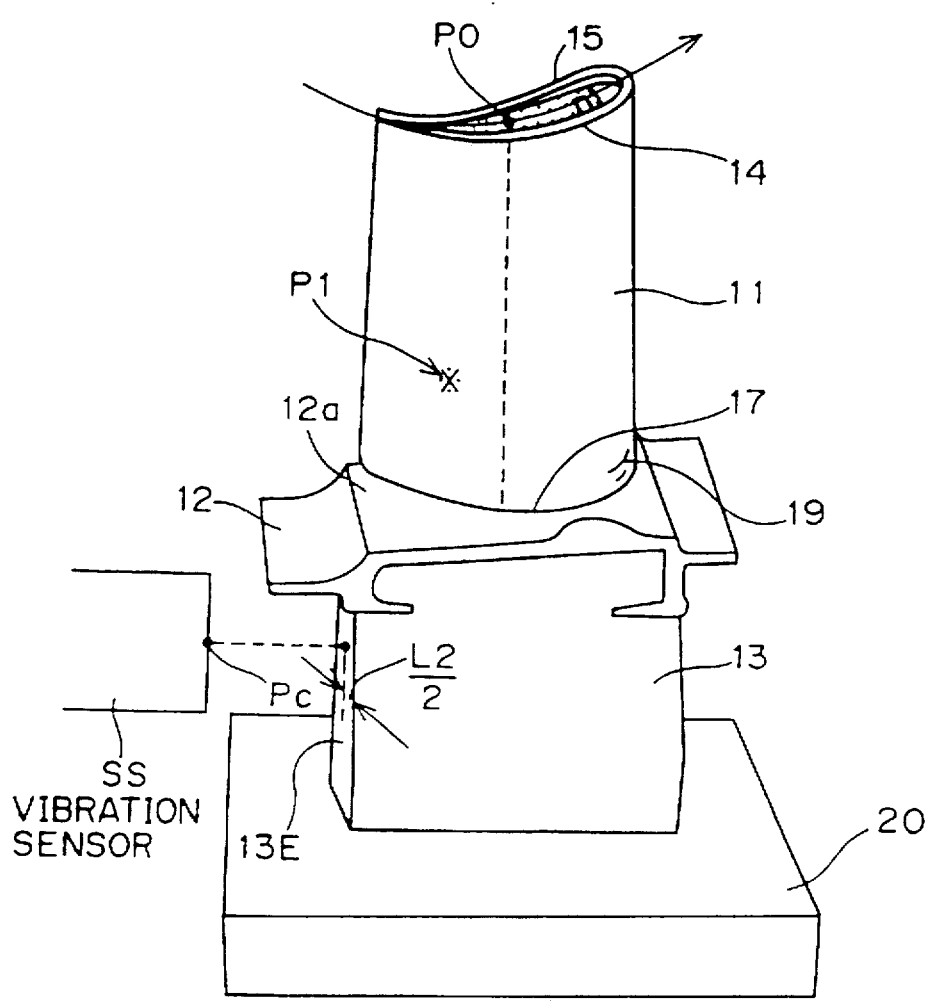
FIG. 5 is a view illustrating an example of the position of a defect that will occur in an object to be measured in accordance with the present invention and the position the arrangement of a vibration sensor.

If there is a scar only in the platform part 12 of this turbine blade or a scar in the leg part 13, it does not present a problem so much. However, a defect, such as a crack 19 as shown in FIG. 5, is formed at the intersection part 17 between the platform part 12 and the blade part 11, the bonding force of the bonding section including the intersection part 17 between the blade part 11 and the platform part 12 becomes weak, leading to a possibility of breakage.

In this invention, an object to be measured, such as the above-described turbine blade, is vibrated, for example, by an impact technique and the resulting vibration waves are picked up by a vibration sensor in a noncontact manner. The picked-up vibration waves are subjected to a spectral analysis and it is detected whether or not there is a defect at the intersection part 17.

Further, a change in thickness of the plate part 14 and the plate part 15 which are equal in thickness in the original state is detected by similarly subjecting the vibration waves picked up to a spectral analysis.

In the case wherein the absence or presence of a defect at the intersection part 17 is detected or a change in thickness of the plate part 14 and the plate part 15 is detected, the part of the blade part 11 of the turbine blade is vibrated. In this example, as the vibration method, a technique of applying an impact is employed. The place where the vibrations are caused is the place where the flexural vibration mode and the torsional vibration mode are generated for the blade part 11.

As shown in FIG. 5, if the blade part 11 is vibrated on the line segment (shown in dotted line in the drawing) passing through the center position PO of the cross section second order moment of the blade part 11, only vibration waves of the flexural vibration mode are generated. Further, if the blade part 11 is vibrated at the center of gravity, vibration waves of the flexural vibration mode are not generated. Accordingly, in this embodiment, the blade part 1 is vibrated at a position except these positions. For instance, the blade part 11 is vibrated at the position shown by a point P1 by applying an impact. Herein, in the application of vibrations, the turbine blade, i.e., an object to be measured, is placed on a cushioning material 20.

On the other hand, a vibration sensor SS is arranged in opposition to a one end surface 13E of the leg part 13 in the direction of the curved surface of the blade part 11. Further, in this case, the center position Pc of the vibration sensor SS is arranged in register with the center position of the thickness L2 of the end surface 13E of the leg part 13. Further, the center position Pc of the vibration sensor SS is positioned, for example, about 15 mm below from the lower end of the platform part 12.

By the impact vibrations, in the blade part 11 are generated vibration waves of the flexural vibration mode, vibration waves of the torsional vibration mode, and stationary vibration waves which are a mixture of vibration waves of the flexural vibration mode and vibration waves of the torsional vibration mode as described before.

Figure 6:
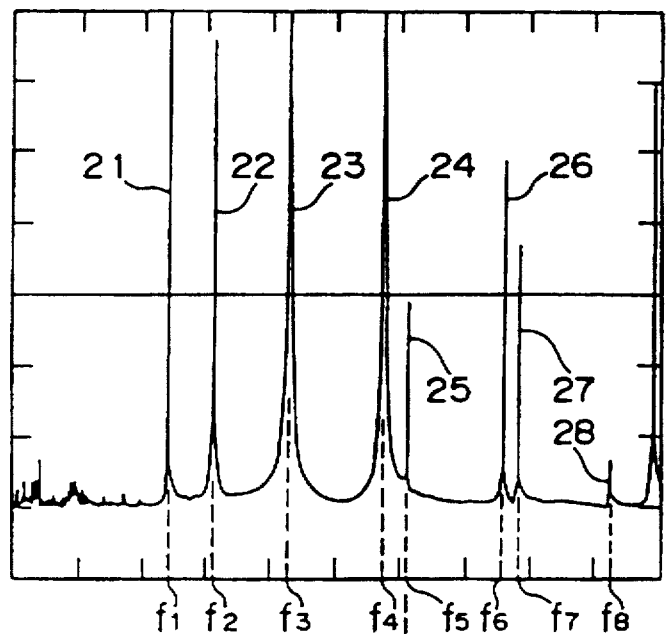
FIG. 6 is a chart showing the spectrum distribution of stationary vibration waves of a case of an object to be measured that is free of defects.

When the vibration waves are picked up by the vibration sensor SS that is very high in directivity and are subjected to a spectral analysis, and if there is, in the intersection part 17, no scar reaching the blade part 11, peaks 21, 22, 23, 24, 25, 26, 27, 28 of spectra are obtained at frequency positions corresponding to the components of the above modes of vibration and the size of the turbine blade as shown in FIG. 6.

Letting the frequencies of peaks 21 to 28 of the spectra be named f1, f2, f3, f4, f5, f6, f7, and f8 in ascending order of the frequencies, the group of frequencies f1 to f3 of the spectra can be designated a first-order spectrum group and the group of frequencies f4 to f7 can be designated a second-order spectrum group. The spectra of the frequency f1 and the frequency f4 are attributed to the flexural vibration mode, the spectra of the frequency f2 and the frequency f5 are attributed to the torsional vibration mode, and the spectra of the frequency f3 and the frequencies f6 and f7 are attributed to the mixture (mainly torsional type vibrations) of the flexural vibration mode with the torsional vibration mode.

Herein, the group of the spectra 24 to 27 of the frequencies f4 to f7 are components that are generated because of that the blade part 11 is composed of the plate part 14 and the plate part 15 and generally the lateral sizes of the plate part 14 and the plate part 15 of the blade part 11 (in this case, the lengths of the curves of the curved surfaces of the plate parts 14 and 15) are different. In the case wherein the blade part 11 is not composed of two plate parts but composed of one plate, the group of the spectra 21 to 23 are generated, but the group of the spectra are not generated.

Further, an object to be measured wherein the part between the plate part 14 and the plate part 15 has no space but is filled with other material is also subject to the present invention.

Figure 7:
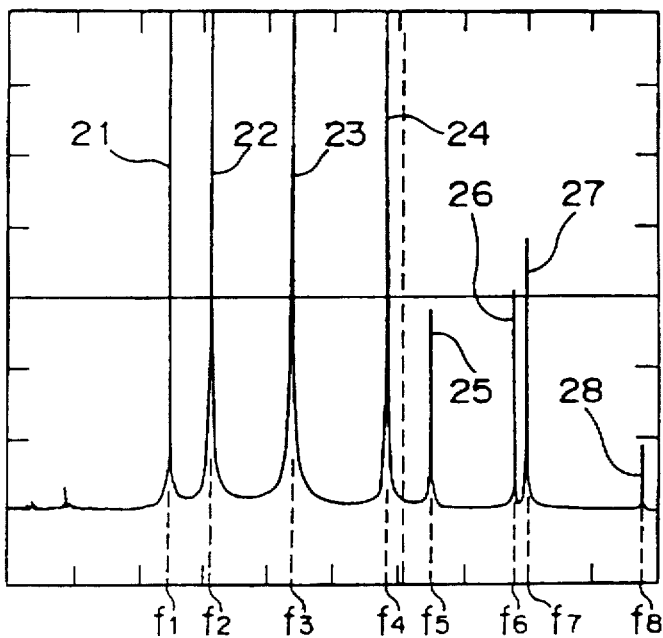
FIG. 7 is a chart showing the spectral distribution of stationary vibration waves of a case of an object to be measure that has a defect.

In the case wherein there is a scar 19 in the intersection part 17 reaching the blade part 11 as shown in FIG. 5, when the blade part 11 is vibrated at the position P1 by applying an impact and the stationary vibration waves generated in the object to be measured are subjected to a spectral analysis, the frequencies f1 to f8 of the peaks 21 to 28 of the above spectra are at the frequency positions shown in FIG. 7.

Herein, comparing FIG. 7 with FIG. 6, since the frequencies f1 and f4 of the first-order spectrum 21 and the second-order spectrum 24 due to the flexural vibration mode are dependent on the size of the object to be measured, the frequencies are little different from the frequencies in the case wherein there is no defect. That is, the frequency f1 or f4 of the first-order spectrum or the second-order spectrum of the flexural vibration mode are not related to the absence or presence of a defect and are approximately constant. In contrast, the frequency difference $\Delta f25$ between the frequencies f2 and f5 of the first-order spectrum and the second-order spectrum of the torsional vibration mode is larger than the frequency of the case having no defect.

Further in this case, although the frequency f2 of the first-order spectrum 22 of the torsional vibration mode is little different from the frequency of the case having no defect, the frequency f5 of the second-order spectrum of the torsional vibration mode is displaced to the relatively higher frequency side due to the presence of the crack 19 in comparison with the case having no crack in FIG. 6.

Accordingly, to detect whether or not there is a defect formed in the intersection part 17, it is possible to detect the defect by finding the frequency difference $\Delta f45$ (=f5−f4) between the frequency f4 of the second-order spectrum of the flexural vibration mode and the frequency f5 of the second-order spectrum of the torsional vibration mode and comparing it with the previously determined reference value of the object to be measured that is free from a defect in the intersection part.

However, this frequency difference neither generalizes precisely and quantitatively a defect in an object to be measured nor quantitates the size of the defect. Therefore, the following operational formula (1) is used:

$$Rf = (f5 - f4)/(f2 - f1) \tag{1}$$

According to the operational formula (1), a defect can be represented quantitatively. Further, it has been ascertained that the ratio value Rf obtained from the operational formula (1) is approximately proportional to the size of a defect 19 formed in the intersection part 17.

In the meantime, the turbine blade that is an object to be measured in this embodiment will be made eventually decreased in thickness of the turbine blade owing to the passage of hot air through the hollow parts in the blade part 11 in use that, for example, scrapes the inner wall surfaces of the hollow parts of the plate parts 14 and 15. It has been made clear that when the thickness of the plate parts 14 and 15 is decreased in this way, it affects the above frequencies f1 to f6, and therefore under such circumstances, the above operational formula for detecting a defect cannot make a precise judgement in some cases.

That is, according to the research made by the inventors of this invention, it has been made clear that even if the thickness of the plate parts 14 and 15 is changed, the frequencies f1 and f4 of the first-order spectrum 21 and the second-order spectrum 24 due to the vibration waves of the flexural vibration mode are changed little because they are dependent on the size of the area of the plate surfaces of the plate part 14 and the plate part 15 whereas the frequencies f2, f3, f5, and f6 as well as the frequency f7 of the spectra due to the torsional type vibrations are shifted to toward lower frequencies as the thickness of the plate parts is decreased.

Therefore, it has been made clear that whereas the frequency difference between the frequencies f1 and f4 is not changed, the frequency difference between the frequency f1 and the frequency f3 and the frequency difference between the frequency f4 and the frequency f6 become small as the thickness of the plate parts 13 and 15 is decreased. As a result, there is a risk that the above operational formula (1) cannot detect precisely a defect 19, if any, formed at the intersection part 17 because it is affected by a change in thickness of the plate parts 14 and 15.

Thus, in the case of an object to be measured wherein the thickness of the plate parts 14 and 15 is changed as in a turbine blade, instead of the above operational formula (1), the following operational formula (2):

$$\{(f5-f4)/(f2-f1)\}/\{(f6-f4)/(f3-f1)\} \quad (2)$$

is used to detect quantitatively a defect.

That is, in the operational formula (2), the term (f6−f4)/(f3−f1) is a component corresponding to a change in thickness of the plate parts 14 and 15, thus when the thickness of the plate part 14 is equal to the thickness of the plate part 15, its value is "1", and by this term the operational result of the operational formula (1) is normalized to enable the influence of a change in the thickness of the plate parts 14 and 15 to be eliminated in the detection of a defect.

Next, a difference in thickness between the plate part 14 and the plate part 15 can be detected as follows. That is, it is assumed that the peak 23 of the spectrum of the frequency f3 is the component at the time of the transition from the vibrations of one of the plate part 14 and the plate part 15 to the longitudinal vibrations of the other plate part and the peaks 26 and 27 of the spectra of the frequency f6 and the frequency f7 are the components at the time of the transition from the vibrations of one of the plate part 14 and the plate part 15 to the harmonic vibrations of the other plate part.

The reason why the frequencies of the spectra of the torsional type vibrations that are a mixture of the torsional vibration mode and the flexural vibration mode is divided into the frequency f6 and the frequency f7 is that, in two-order or more higher-order vibrations, based on a difference in thickness between the plate part 14 and the plate part 15, the frequency of the torsional type vibrations begins to become different.

Figure 8:
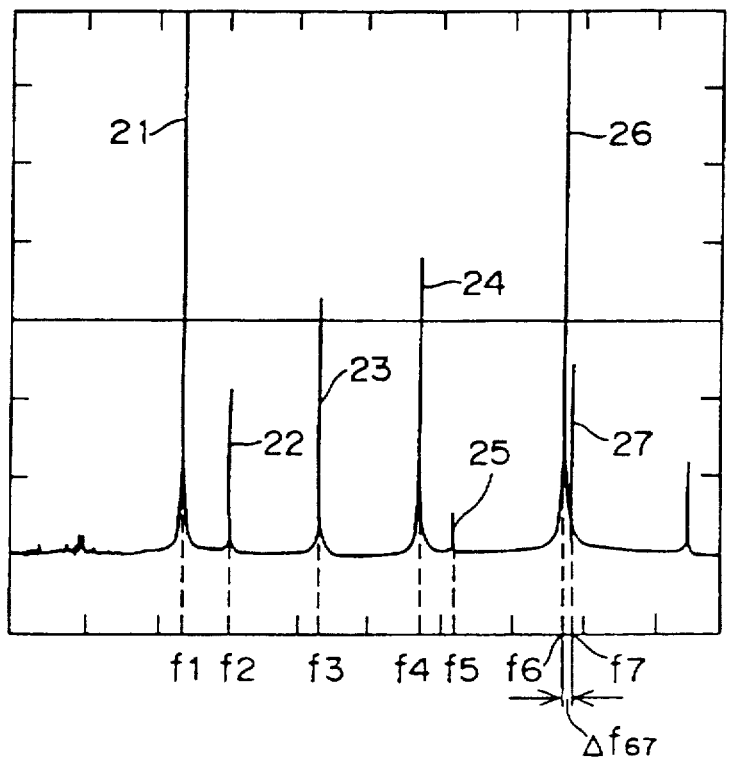
FIG. 8 is a chart showing the spectrum distribution of stationary vibration waves of a case wherein two plate parts of an object to be measured are arranged with the plate surfaces of the plate parts opposed to have a prescribed space between them and the difference between the thicknesses of two plate parts is small.
Figure 9:
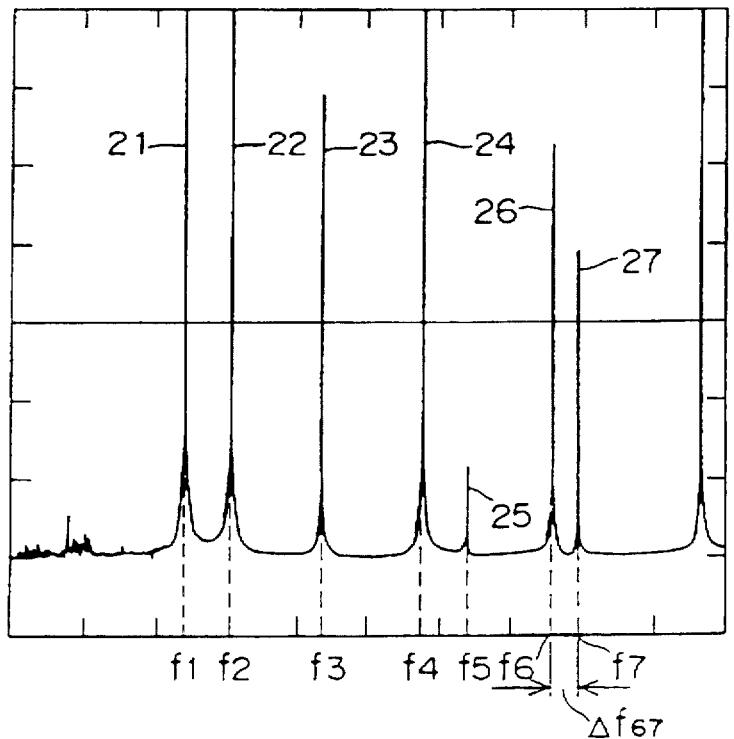
FIG. 9 is a chart showing the spectral distribution of stationary vibration waves of a case wherein two plate parts of an object to be measured are arranged with the plate surfaces of the plate parts opposed to have a prescribed space between them and the difference between the thicknesses of two plate parts is large.

FIG. 8 shows the spectral distribution of stationary-vibration waves at the time when a turbine blade in the initial state where the thicknesses of the plate part 14 and the plate part 5 are not very different is vibrated and FIG. 9 shows the spectral distribution of stationary-vibration waves at the time when a turbine blade is vibrated that is in a state wherein the inner wall surfaces of the plate part 4 and the plate part 15 are peeled by the use and the difference in thickness between the plate part 14 and the plate part 15 is made great.

Herein, in FIG. 8 and FIG. 9, when the differences Δf67 between the frequency f6 and the frequency f7 are compared, it can be realized that the frequency difference Δf67 in FIG. 9 in the case wherein the difference in thickness between the plate part 14 and the plate part 15 has become large is larger than the frequency difference Δf67 in FIG. 8 in the case wherein there is no difference in thickness between the plate part 14 and the plate part 15. In this embodiment, in order to quantitate this frequency difference Δf67, the value normalized by the frequency f6 is used. That is, it is represented by $$Ig=(f7-f6) \quad (3)$$

wherein Ig stands for the index indicating the relative difference in thickness between the plate part 14 and the plate part 15.

It can be understood that the greater the index Ig is, the greater the difference in thickness between the plate part 14 and the plate part 15 is. As described earlier, if a turbine blade is a good one and in the original state, since the thicknesses are equal, then when the index Ig is large, it means that the peeling caused by a crack formed mainly in the inner wall surface of the plate part 14 or the plate part 15 is large, which detects substantially the formation of a crack.

Incidentally, of course the detection can be made which includes the case wherein, instead of the inner wall surfaces of the plate parts 14 and 15, the outer wall surfaces are scraped to change the thickness of the plate parts 14 and 15.

Even in the case wherein a difference in thickness between the plate part 14 and the plate part 15 is detected, as described before, when the thickness of the plate part 14 and the plate part 15 is decreased, the frequencies f1 and f4 of the first-order spectrum 21 and the second-order spectrum 24 due to the vibration waves of the flexural vibration mode are little different, but since the frequencies f2, f3, f5, and f6 as well as the frequency f7 of the spectra due to the torsional type vibrations are shifted toward lower frequencies, there is a risk that a difference in thickness between the plate part 4 and the plate part 5 cannot be assessed precisely and quantitatively.

Therefore, in this embodiment, instead of the index Ig represented by the above operational formula (3), an index IG represented by the following operational formula (4):

$$IG=\{(f7-f6)/f6\}+\{(f6-f4)/(f3-f1)\} \quad (4)$$

is used to assess quantitatively a difference in thickness between the plate part 14 and the plate part 15.

That is, in the operational formula (4), the term (f6−f4)/(f3−f1) is the component of the ratio of the thicknesses of the plate parts 14 and 15, thus when the plate part 14 and the plate part 15 are equal in thickness, that value is "1", and by this term the result of the operation of the operational formula (3) is normalized to enable the influence of a change in thickness of the plate part 14 and the plate part 15 to be eliminated.

Now, the method of predicting the life of a turbine blade, an object to be measured, is described.

For a turbine blade, mainly the blade part 11 is used and the blade part 11 will be deteriorated. Therefore, it is important to know deterioration in this blade part 11. In this embodiment, in order to know deterioration in the blade part 11 of this turbine blade, the turbine blade is vibrated and the vibration waves are subjected to a spectral analysis. The position where the vibrations are caused is not at the blade part 11 but is at a prescribed position of the platform part 12 or the leg part 13 where longitudinal waves are generated without fail.

Figure 10:
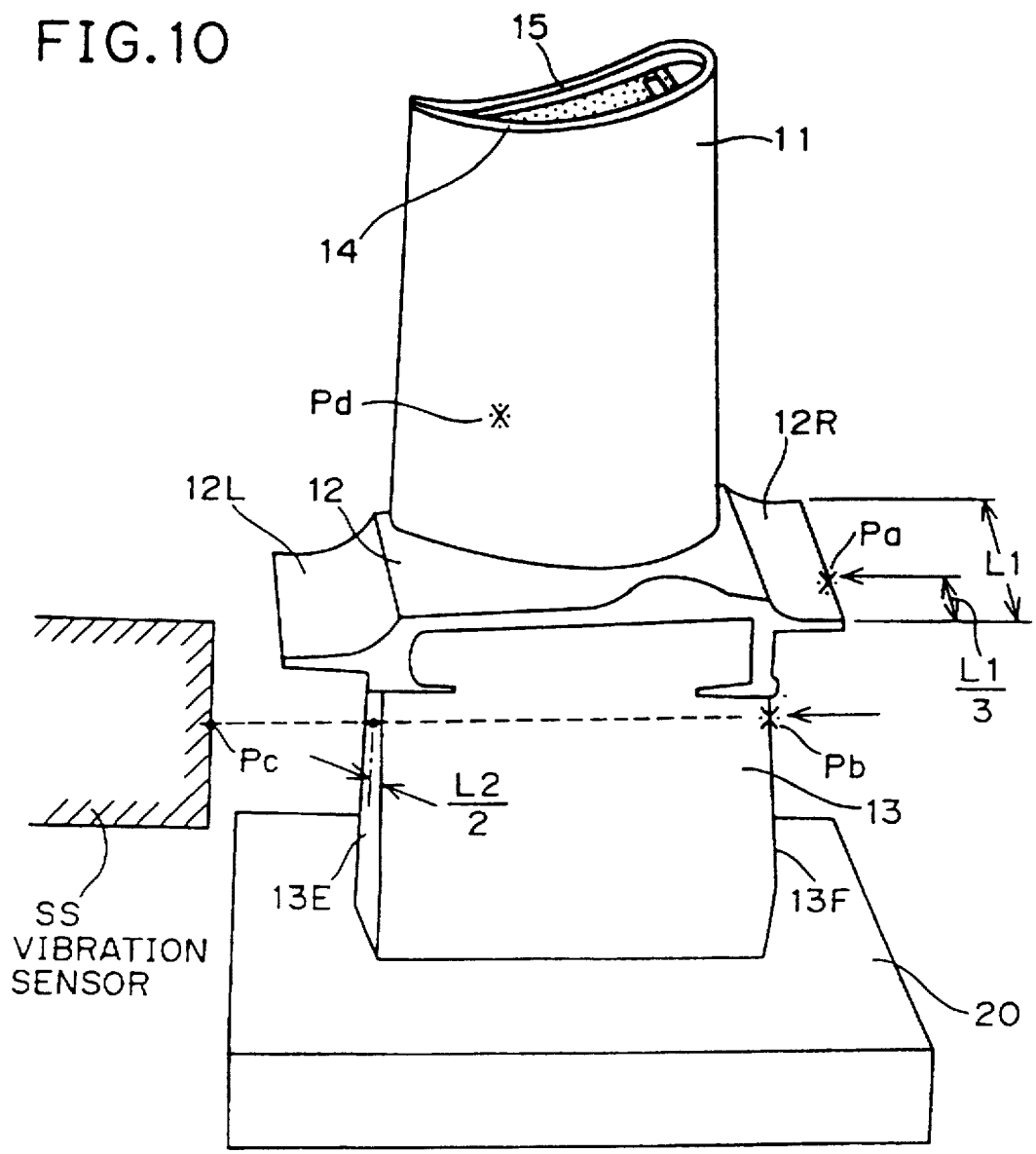
FIG. 10 is a view illustrating a position where an object to be measured is vibrated in an embodiment of the present invention.
Figure 11:
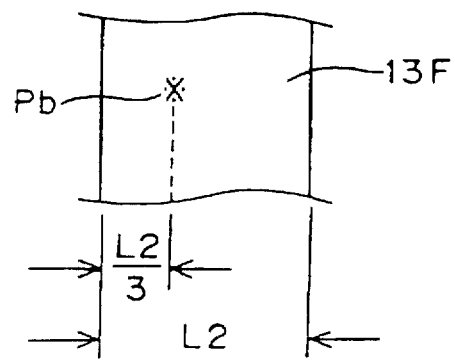
FIG. 11 is a view illustrating a position where an object to be measured is vibrated in an embodiment of the present invention.

FIG. 10 and FIG. 11 are views illustrating the position where the turbine blade is vibrated and an example of the arrangement of a vibration sensor, such as a microphone, for picking up vibration waves of the turbine blade when vibrations are caused at that position.

In FIG. 10, the position Pa is an example of the vibration application position where the platform part 12 is vibrated. That is, as shown in the drawing, this position Pa is present in one of lip parts 12R and 12L, i.e., the lip part 12R, that are extended to the right and left orthogonally to the direction of the thickness of the blade part 11 of the platform part 12. In the case of this example, letting the length of the lip part 12R in the direction of the thickness of the blade part 11 be L1, the vibration application position Pa is at a distance of L1/3 from the end of the lip part 12R on the convex side of the blade part 11. Vibrations are caused by applying, for example, an impact to this position Pa from the extended direction of the lip part 12R as shown by the arrow in FIG. 10.

On the other hand, the vibration sensor SS is arranged on the side of the lip part 12L opposite to the lip part 12R. In the case of this example, the vibration sensor SS is arranged in opposition to the end surface 13E on the side of the lip part 12L of the leg part 13. Further, in this case, the center position Pc of the vibration sensor SS is arranged in register with the center position of the thickness L2 of the end surface 13E of the leg part 13 and the center position Pc of the vibration sensor SS is positioned, for example, about 15 mm below from the lower end of the lip part 12L, similarly to the case in FIG. 5. In other words, the position of the vibration sensor SS is the same position as the position in FIG. 5 described above.

Further, in FIG. 10, the position Pb is the case of the vibration application position wherein vibrations are caused at the leg part 13. That is, as shown in FIG. 11, this position Pb is in the end surface 13F on the side of the lip part 12R of the platform part 12 of the leg part 13 and is a position below the lip part 12R approximately in register with the center position Pc of the vibration sensor SS. Further, as shown in FIG. 11, in the case of this example, letting the length of the leg part 13 in the direction of the thickness of the blade part 11 be L2, the vibration application position Pb is at a distance of L2/3 from the end of the leg part 13 on the convex side of the blade part 11.

Further, vibrations are caused by applying, for example, an impact to this position Pb from the extended direction of the lip part 12R as shown by the arrow in FIG. 10. In this case of the vibration application position Pb, the position of the vibration sensor SS may be similar to that shown in FIG. 10.

When the results obtained by vibrating the turbine blade at these positions Pa and Pb, picking up the vibration waves by the vibration sensor SS, and subjecting the vibrations to a spectral analysis are compared with the case wherein the part of the blade part 11 is vibrated, for example, at the position Pd, the following is obtained.

That is, the inventors compared the results obtained by carrying out vibrations at the position Pd of the blade part 11 shown in FIG. 10 and carrying out a spectral analysis thereof with the results obtained by carrying out vibrations at the above positions Pa and Pc and carrying out a spectral analysis thereof. Herein, the position Pd is a position where the flexural vibration mode (longitudinal waves) and the torsional vibration mode will occur and that excepts the position of the center of gravity of the blade part 11 and also excepts the center position of the cross section second-order moment of the blade part 11.

Figure 12:
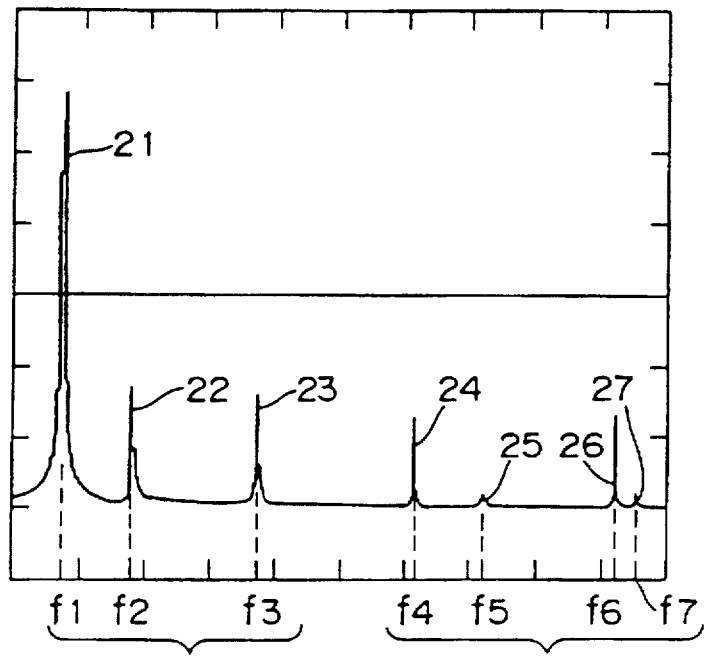
FIG. 12 is a chart illustrating the spectrum distribution of stationary vibration waves obtained when a major working part of an object to be measured is vibrated.

FIG. 12 is a spectrum distribution of the case wherein vibrations are caused at the position Pd in the blade part 11. That is, in a similar way as described above, peaks 21, 22, 23, 24, 25, 26, and 27 of spectra are obtained at frequency positions corresponding to the components of the vibration modes described above.

Further, the spectrum of the frequency f8 not appearing in FIG. 12 is the second-order component of longitudinal waves generated when the plate part 14 and the plate part 15 are not divided but formed into one plate and it constitutes longitudinal waves as compressional waves described above. However, as analogized from FIG. 12, spectra of an order higher than this are damped considerably and is difficult to be detected because the energy of the first-order spectrum 21 of the frequency f1 is large. Figures of spectra of the frequency f8 or higher in order than that are omitted in this case.

Figure 13:
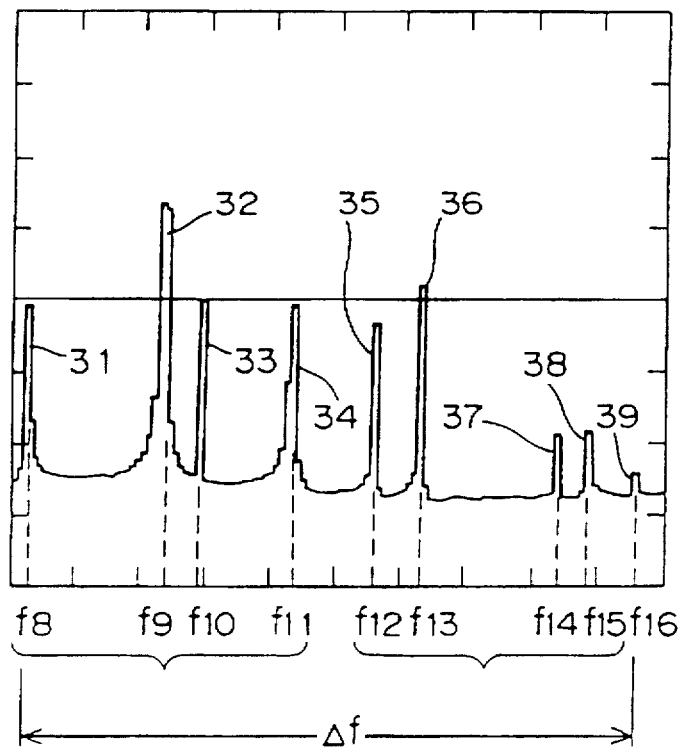
FIG. 13 is a chart illustrating the spectrum distribution of a higher order of stationary vibration waves that is obtained when an object to be measured is vibrated in accordance with the method of the present invention.

In contrast, in the case wherein vibrations are caused not at the blade part 11 but at the position Pa of the platform part 12 or at the position Pb of the leg part 13, a spectrum component at the above frequency f8 or a higher frequency can be relatively stably obtained. An example of the spectrum distribution of the frequency f8 or a higher frequency at that time is shown in FIG. 13. Incidentally, the spectrum distribution of the frequencies f1 to f7 at the vibration application position Pa or Pc are omitted and are not shown.

In FIG. 13, peaks 31 to 39 of 9 spectra of frequencies of f8 to f9 are obtained, and out of them the spectrum 31 of the frequency f8 and the spectrum 39 of the frequency f16 are the second-order and third-order components of longitudinal waves generated when the plate part 14 and the plate part 15 are not separated but are formed into one plate. Further, the spectrum 31 of the frequency f8 to the spectrum 34 of the frequency 11 are the spectrum group attributed to one of the plate part 14 and the plate part 15 and the spectrum 35 of the frequency f12 to the spectrum 38 of the frequency f15 are the spectrum group attributed to the other of the plate part 14 and the plate part 15.

In this specification, for the sake of description, hereinafter, hereinafter the spectrum of the frequency f8 is called the second-order spectrum of longitudinal waves and the spectrum of the frequency f16 is called the third-order spectrum of longitudinal waves.

Figure 14:
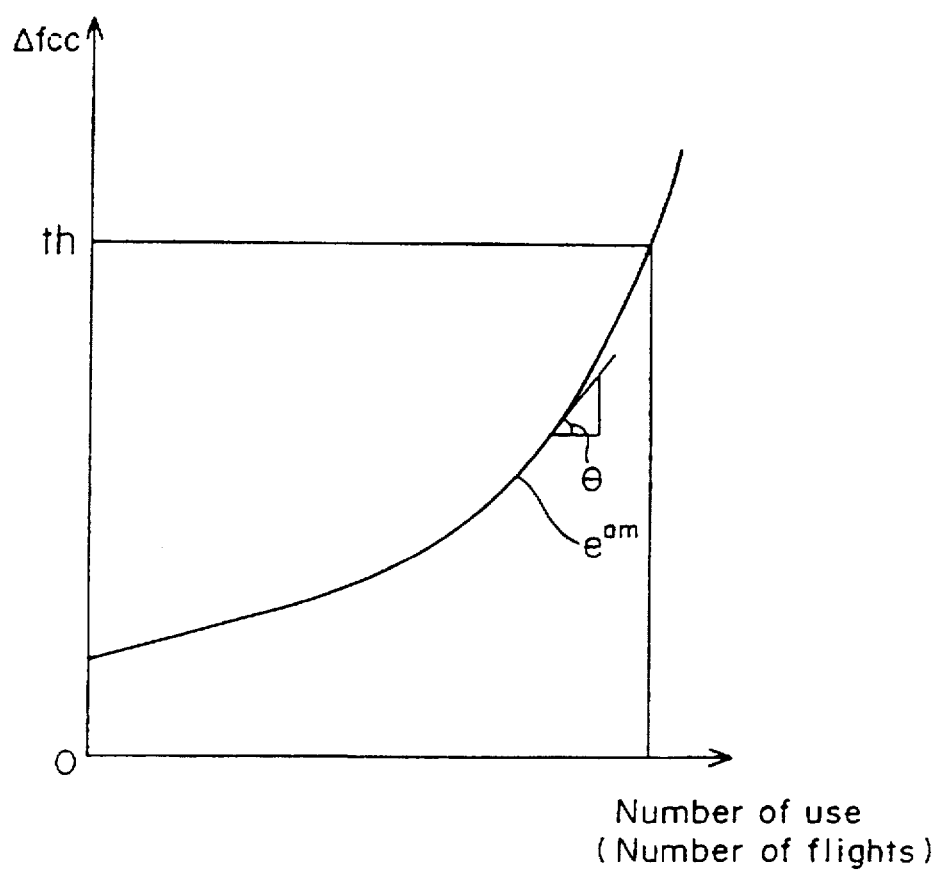
FIG. 14 is a chart showing an example of a life predicting curve that is used in a life predicting apparatus according to the present invention.

As described above, the inventors of this invention have measured the relationship between the difference Δfcc (=f16−f8) between the frequency f8 of the second-order spectrum of longitudinal waves and the frequency f16 of the third-order spectrum of longitudinal waves with the number of use of a turbine blade, such as the number of so-called flights of an airplane, or the operating time of an airplane, such as the flight time, and have found a relation curve as shown in FIG. 14. The function of this curve is an exponential function represented by $$\Delta fcc = \exp(am) \quad (5)$$

wherein the constant a is a value which is in conformity with the size of the turbine blade and can be easily determined by actually measuring the turbine blade, and m is the number of use or the operating time, which is the number of flights in this example. Hereinafter this curve is called a curve for predicting the life.

That is, as shown by the curve for predicting the life in FIG. 14, as the number of use of a turbine blade is increased and the turbine blade is deteriorated, the frequency difference Δfcc is increased exponentially. It has been made clear that, on this exponential curve, if the frequency difference Δfcc exceeds a prescribed threshold value th, a defect, such as a crack, is eventually generated in the turbine blade.

In this case, the threshold value is determined for the tangent of the inclination θ of the curve for predicting the life (see FIG. 14), i.e., the tan θ , and the frequency difference Δfcc at the time when the value of tan θ exceeds a predetermined value becomes the above threshold value th.

From the above, by vibrating a turbine blade after its use by a vibration application technique, such as an impact technique, at the position Pa of the platform 12 described above or at the position Pb of the leg part 13, picking up the resulting vibrations, subjecting the vibrations to a spectral analysis, finding the above-described frequency difference Δfcc, and examining where the frequency difference Δfcc is located on the above-described life predicting curve, the life of the particular turbine blade can be predicted as to how many times or how many hours the turbine blade can be used to the threshold value th even if the actual number of use (the actual number of flights) is not known.

Next, an embodiment of an apparatus to which the above-described method is applied is described with reference to the drawings.

Figure 15:
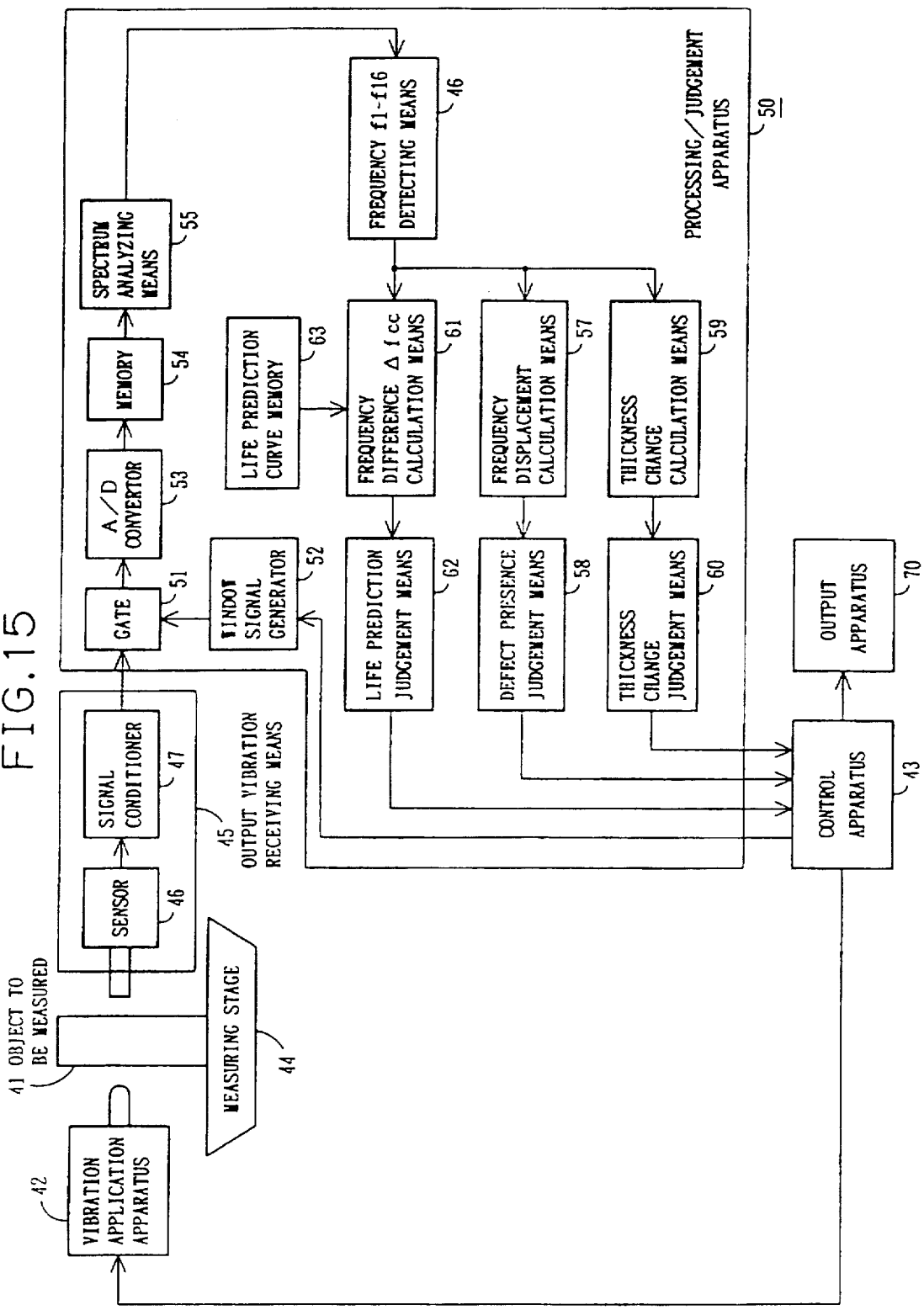
FIG. 15 is a block diagram showing the constitution of an apparatus according to the present invention.

FIG. 15 shows an embodiment of the apparatus of this example, wherein 41 indicates an object to be measured, which is a turbine blade in this example. The object-to-be-measured 41 is placed on a measuring stage 44 equipped with a cushioning material 20 (not shown in FIG. 15) as shown in the drawings illustrating vibration application apparatuses of FIG. 5 and FIG. 10. 42 indicates a vibration application apparatus, and 43 indicates a control apparatus having, for example, a microcomputer.

The control apparatus 43 drives the vibration application apparatus 42 to vibrate the turbine blade that is the object-to-be-measured 41 at the vibration application position P1 shown in FIG. 5 described above in the case of detecting a defect at the intersection part 17 of the object to be measured and detecting a difference in thickness between the plate part 14 and the plate part 15. Further in the case of predicting the life of the turbine blade, the turbine blade that is the object-to-be-measured 41 is vibrated at the vibration application position Pa or the position Pb shown in FIG. 11.

In this example, the vibration application apparatus 42 gives an impulse to the object-to-be-measured 41, for example, by impacting it by an impacter, such as a weight, in a pendulous fashion, for example. The mechanism for driving the weight is constituted to have a cam mechanism or the like so that after giving an impulse the weight may be moved away from the object to be measured instantly. The application of the vibrations may be given several times instead of once. In the case of predicting the life, the vibrations may be caused at both positions Pa and Pb instead of at the same position.

The vibrations of the object-to-be-measured 41 that has been vibrated in the above manner are detected by the vibration sensor 46 of an output vibration receiving apparatus 45 in a noncontact manner and are converted into electric signals, which are subjected to prescribed signal processing at a signal conditioner 46. The sensor 46 is arranged at the position of the sensor SS shown in FIG. 5 and FIG. 11. As this sensor 46, any one can be used so long as it can detect vibrations and a displacement meter or the like can be used. Of course one having a keen directivity in the direction toward the object-to-be-measured 41 is preferable in order not to pick up ambient noise vibrations as far as possible.

In the signal conditioner 47, the electric signals are amplified and, for example, the elimination of unnecessary high and low region components (the elimination of trend) is carried out.

The electric signals from the output vibration receiving apparatus 44 are fed to a processing/judgement apparatus 50. The processing/judgement apparatus 50 has, for example, a microcomputer, and carries out processing and judgement operation, which are described later, by software, which processing is shown in FIG. 15 by means of functional blocks.

Incidentally, the vibrations that are handled here are vibrations inherent in the shape of the particular object to be measured. When an object to be measure is vibrated forcibly, however the forced vibrations and the like will be present as a mixture with natural vibrations (longitudinal vibrations as stationary waves). Therefore, it is desirable to remove these except natural vibrations as far as possible. In this example, this demand is satisfied as follows.

For the forced vibrations, the measurement of the signals from the sensor 45 is started at a point after the passage of a prescribed period from the application of vibrations, so that the influence is removed. That is, when the object-to-be-measured 41 is vibrated by an impulse impacting method, the measurement is started at a point after a little passage of a period immediately after the application of vibrations by impacting or the like.

In this case, the period from the impacting to the start of the measurement can be determined as follows. That is, the velocity c of sound waves propagating through the object-to-be-measured 41 varies depending on its Young's modulus E (coefficient of elasticity) and the density ρ of the object and has the relationship:

$$c^2 = E/\rho$$

Figures 16A, 16B:
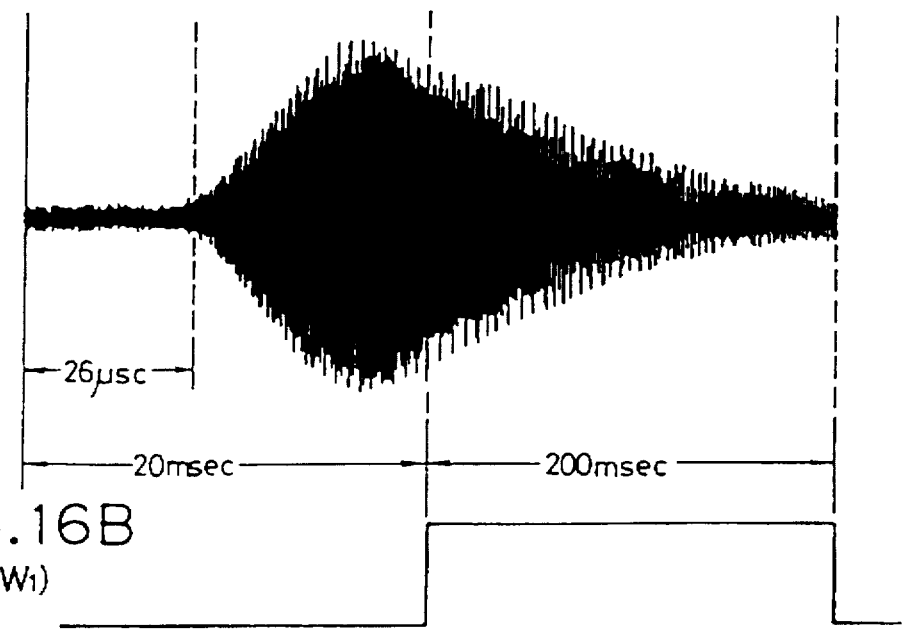
FIGS. 16A and 16B are charts illustrating the action of a circuit of a part of FIG. 15.

Further, for instance, in the case of this impulse impacting method of this example, the time series waveform of the vibrations picked up from immediately after the impact application is as shown in FIG. 16A.

As can be understood from this waveform of FIG. 16A, since the vibrations after the application of vibrations is the same as the case of seismic waves, the vibrations include longitudinal waves having a high velocity and waves having a low velocity as described above, and has remaining forced vibrations, so that the waveform is not the natural vibration waveform peculiar to the shape of the object-to-be-measured 41. Thus, it is assumed that the natural vibration waves peculiar to the shape is observed a little before the stoppage, for example, as in the case of "precession" of a top. Therefore, a window W1 having a rectangular wave as shown in FIG. 16B is set and by this window W1, the vibration waves are extracted in this example.

That is, the electric signals inputted in the processing/judgement apparatus 50 are fed to a gate means 51. Then, the natural vibration component of the shape of the object-to-be-measured 41 is extracted from the vibrations of the object-to-be-measured 41 after the application of vibrations, i.e., the impacting, by the above window signal W1 from a window W1 forming means 52. In the window forming means 52, the information of the start of the application of vibrations from the control apparatus 43 is received and the period from immediately after the impacting to the point of the rise of the window W1 and the window width are set up. In the example shown in FIGS. 16A and 16B, the window W1 is risen at a point after passage of 20 sec immediately after the impacting and a window width of 200 msec is set up.

As described above, by the window W1, the natural vibration component of the shape of the object-to-be-measured is extracted. Further, the natural vibration part is converted to a digital data by an A/D converting means 53 and is written into a memory means 54. Then, the digital data from the memory means 54 is read out and is fed to a spectrum analyzing means 55 to analyze the spectra.

The results of the spectral analysis by the spectrum analyzing means 55 are fed to a frequency-f1-to-f16 detecting means 56. In the frequency-f1-to-f16 detecting means 56, peaks 21 to 27 and 31 to 39 of the above spectra are detected from the spectra obtained in the spectrum analyzing means 45 to find the frequencies f1 to f16. With respect to the above peaks 21 to 27 and 31 to 39 of the spectra, peaks of the spectra are detected successively in descending order of the values within a predetermined frequency range, for example, within a frequency range less than 20 kHz, and are determined as the peak 21, the peak 22, and so on in ascending order of the frequencies. Then, the frequencies f1, f2, and so on are found.

The frequencies f1 to f7 out of the frequencies f1 to f16 found by the detecting means 56 are fed to a frequency displacement calculation means 57 for calculating the frequency displacement of the spectra of the torsional vibration mode.

In this frequency displacement calculation means 57, the operational formula (1) or the operational formula (2) described above is worked. In this embodiment, the operational formula (2) is worked.

Then, the results of the operation are sent to a defect present judgement means 58, where it is judged whether or not a defect is present, and the size of the defect, if any, is judged. Then, the results of the judgement are sent to the control apparatus 3.

The control apparatus 43 sends the results of the judgement to an output means 70. The output means 70 displays the information including the presence or absence of a defect and the size of the defect obtained by the results of the judgement on a display, prints out on a sheet of recording paper, or makes them known in an audio manner.

The information of the frequencies f1, f3, f4, f6 and f7 out of the frequencies f1 to f16 found by the frequency detecting means 56 is fed to a thickness change calculation means 59 for calculating the difference in thickness between the plate part 14 and the plate part 15, where the operational formula (4) described above is worked. That is, in the thickness change calculation means 59, the frequency difference Δf67 between spectra divided into two by high-order vibrations of torsional type vibrations as described above, i.e., between the frequency f6 and the frequency f7 in this example, is calculated and in order to normalize the calculated value, the operational formula (4) is worked. Incidentally, as described above, the operational formula (3) may be worked by using only the information of the frequencies f6 and f7.

The results of the calculation by the thickness change calculation means 59 are fed to a thickness change judgement means 60, where a difference in thickness between the plate part 14 and the plate part 15 of the turbine blade is judged. This judgement is such that if the value IG resulting from the operational formula (4) is, for example, a prescribed value or over, the object to be measured is judged to be defective, or a defect is formed in the object to be measured. The result of the judgement and the value IG resulting from the operation by the thickness change calculation means 59 are sent to the control apparatus 43.

The control apparatus 43 sends the above IG and the above result of the judgement to an output means 70. The output means 70 displays the information of the above IG and the result of the judgement on a displayer, prints out on a sheet of recording paper, or makes them known in an audio manner.

By the display or printing-out of the output means 70, the formation of a defect of the inner wall surface of the plate part 14 or the plate part 15 due to a defect and a change in thickness of the plate part 14 or the plate part 15 due to that defect can be known quantitatively.

Further, the information of the frequencies f8 and f16 out of the frequencies f1 to f16 found by the frequency detecting means 56 are fed to a frequency difference Δfcc calculation means 61. The frequency difference Δfcc calculation means 61 calculates the frequency difference Δfcc between them (=f16–f8). The value of the frequency difference Δfcc thus calculated is sent to a life prediction judgement means 62.

With the life prediction judgement means 62 is linked a life prediction curve memory 63. In this life prediction curve memory 63 is stored information of a plurality of life prediction curves with the constant a with respect to the size of the object to be measured as a parameter. This information also includes the threshold value of the life with the safety factor taken into consideration.

The life prediction judgement means 62 reads, based on the constant a previously given by an operator as a parameter, the information of the life prediction curve of this constant a from the memory 63 and stores it, for example, in a built-in buffer memory.

The life prediction judgement means 62 collates the frequency difference Δfcc calculated by the frequency difference Δfcc calculation means 61 with the life prediction curve stored in the buffer memory and predicts the life with making reference to the threshold value. The life prediction judgement means 62 sends the result of the prediction, for example, the information on the number of remaining usable times or the remaining usable period, to the control apparatus 43.

The control apparatus 43 sends the result of the prediction to an output means 70. The output means 70 displays the information on the usable times or the usable period, i.e., the result of the prediction, on a display, prints out it on a sheet of recording paper, or make it known in an audio manner.

For the apparatus shown in FIG. 15, an operator indicates beforehand a measurement item as to whether a defect that is formed at the intersection part is detected, a measurement item as to whether a difference in thickness between the plate part 14 and the plate part 15 is detected, or a measurement item as to whether the life of an object to be measured is predicted. For that purpose, to the control apparatus 43 are linked a console input means 71 for an operator, such as a keyboard and a mouse. The operator indicates the measurement item required to be measured through this console input means 71.

Upon reception of the input of this indication by the operator, if the measurement item is to detect a defect formed at the intersection part, the control apparatus 43 brings the vibration application position for the turbine blade, i.e., the object to be measured, by the vibration application apparatus 42 to the part of the blade 11 shown in FIG. 5 and operates the frequency displacement calculation means 57 and the defect presence judgement means 58. Upon the reception of the result of the judgement from the defect presence judgement means 58, the control apparatus 43 controls the output to the output apparatus 70 as described above and lets the measurer know the presence or absence of a defect in the intersection part.

If the measurement item is to detect a difference in thickness between the plate part 14 and the plate part 15, the control apparatus 43 brings the vibration application position for the turbine blade, i.e., the object to be measure, by the vibration application apparatus 42 to the part of the blade 11 as shown in FIG. 5 and operates the thickness change calculation means 59 and the thickness change judgement means 60. Upon the reception of the result of the judgement from the thickness change judgement means 60, the control apparatus 43 controls the output to the output apparatus 70 as described above.

Further, if the measurement item is to predict the life of an object to be measured, the vibration application position for the turbine blade, i.e., the object to be measure is brought to the part of the platform part 12 or the leg part 13 shown in FIG. 11 and the frequency difference Δfcc calculation means 61 and the life prediction judgement means 62 are operated. Upon the reception of the result of the judgement from the life prediction judgement means 62, the control apparatus 43 controls the output to the output apparatus 70 as described above.

Incidentally, with respect to the above method of detecting a defect or the like at the intersection part, although the descriptions have been made taking, by way of example, the case wherein a crack is formed in an object to be measured, in a case wherein "a cavity" is formed in an intersection part of an object to be measured and a case wherein a recess is formed in an intersection part of an object to be measured, its presence and its size can be judged in a manner similar to the above. Further, if a part which is harder than other part is locally formed in an intersection part of an object to be measured due to deterioration with age, the part which is different in hardness can be considered as a defect and the presence thereof and its size can be judged.

In the description of the method of predicting the life, although the life of an object to be measured is predicted depending on the frequency difference between the second order spectrum and the third order spectrum of longitudinal waves, if higher spectra can be obtained stably, of course the frequency difference between the higher spectra may be used.

As described above, according to the present invention, an object to be measured is vibrated, the stationary vibration waves generated in this object to be measured are picked up in a non-contact manner, and by analyzing the spectra thereof, a defect formed at an intersection part of the object to be measured can be detected. Accordingly, inconvenience as in the contact-type non-destructive probe method is not brought about and the detection of a defect can be carried out stably and positively.

Further, according to the present invention, an object to be measured is vibrated, the stationary vibration waves generated in this object to be measured are picked up in a noncontact manner, and by analyzing the spectra thereof, a difference in thickness between two opposed plate parts of the object to be measured with a prescribed gap between the two plate surfaces as well as a defect formed not only in the outer wall surface of the plate parts but also in the inner wall surface thereof can be detected.

Further, according to the present invention, an object to be measured that has a first section which is a major working section and a second section united integrally with the first section or bonded to the first section is vibrated at said second section, and by using the fact that the frequency difference between the nth-order spectrum higher than the second order spectrum of the spectra of longitudinal waves out of the stationary wave vibrations and the (n+1)th-order spectrum is changed depending on the degree of deterioration of the object to be measured, said frequency difference is found, so that the life of the object to be measured can be predicted.

In this invention, by vibrating the object to be measured at the second section instead of the first section that is the working section serving as the means of the object to be measured, it is easy to detect a higher order spectrum of longitudinal waves. Since longitudinal waves is difficult to be influenced by a scar or the like and higher the order is, the further difficult it is to be influenced by a scar or the like, according to the present invention, the life of an object to be measured can be predicted stably by using the frequency difference of higher-order spectra.

Further, in the case of the present invention, since, by vibrating an object to be measured and picking up the thus resulting stationary wave vibrations of the object to be measured in a non-contact fashion, the life can be predicted, the object to be measured will not be scarred or is deteriorated for the prediction of the object to be measured as in the case wherein an object to be measured is brought in contact with a sensor.

What is claimed is:

1. A method of detecting a change in the state of a part of an object to be measured that has a section comprising a first plate part and a second plate part which has a plate surface opposite to a plate surface of said first plate part with a gap between said plate surfaces and is integral with said first plate part or is connected to said first plate part, comprising the steps of applying vibrations to said object to be measured at a site at said section to generate flexural, torsional and stationary vibration waves in said object, subjecting the stationary vibration waves generated in said object to be measured to a spectral analysis, calculating the frequency difference of spectra divided into two by high order torsional vibrations generated at said section out of the group of spectra by said stationary vibration waves, and detecting a change in thickness between said first plate part and said second plate part or a defect formed in said first plate part or said second plate part based on the calculated frequency difference.

2. An apparatus for detecting a change in the state of a part of an object to be measured that has a section comprising a first plate part and a second plate part which has a plate surface opposite to a plate surface of said first plate part with a gap between said plate surfaces and is integral with said first plate part or is connected to said first plate part, comprising a vibration application means for applying vibrations to said object to be measured at a site at said section where flexural, torsional and stationary vibration waves are generated, a pick-up means for picking up vibrations of said object to be measured and converting said vibrations into electric signals, a spectral analysis means for receiving the signals from the pick-up means and subjecting the stationary vibration waves generated in said object to be measured to a spectral analysis, a frequency difference calculation means for calculating the frequency difference of spectra divided into two by high order torsional vibrations generated at said section out of the group of spectra by said stationary vibration waves obtained by said spectral analysis means, and a detection means for detecting quantitatively a change in thickness between said first plate part and said second plate part or a defect formed in said first plate part or said second plate part based on the frequency difference calculated by said frequency difference calculation means.

3. The apparatus for detecting a change in the state of a part of an object to be measured as claimed in claim 2, wherein said vibration application means is a means for applying vibrations to said object to be measured by impacting.

4. The apparatus for detecting a change in the state of a part of an object to be measured as claimed in claim 2, wherein said vibration application means is a means for impacting said object to be measured, and a gate means for taking out natural vibrations of said object to be measured after a prescribed time after the application of vibrations is provided between said pick-up means and said frequency displacement detection means.

* * * * *